United States Patent [19]

Campbell

[11] Patent Number: 4,582,907

[45] Date of Patent: Apr. 15, 1986

[54] 2-(2-AMINO-2-THIAZOLIN-4-YL)ACETIC ACID

[75] Inventor: Malcolm M. Campbell, Holcombe, England

[73] Assignee: Pfizer Inc., New York, N.Y.

[21] Appl. No.: 720,822

[22] Filed: Apr. 8, 1985

[51] Int. Cl.$^4$ ............................................ C07D 277/18
[52] U.S. Cl. .................................................... 548/194
[58] Field of Search ........................................... 548/194

[56] References Cited

U.S. PATENT DOCUMENTS 4,072,687  2/1978  Togo ..................... 548/194

OTHER PUBLICATIONS

D. R. Williams and B. W. Halstead, J. Toxicol.: Clin. Toxicol., 19, 1081–1115 (1982–1983).

*Primary Examiner*—Robert Gerstl
*Attorney, Agent, or Firm*—Charles J. Knuth; Albert E. Frost; Paul D. Thomas

[57] ABSTRACT

2-(2-Amino-2-thiazolin-4-yl)acetic acid or a pharmaceutically acceptable acid addition or cationic salt thereof useful in removal of excessive levels of certain metal ions from animals, including humans, and in protection of said animals from exposure to radioactivity.

4 Claims, No Drawings

2-(2-AMINO-2-THIAZOLIN-4-YL)ACETIC ACID

BACKGROUND OF THE INVENTION

The invention relates to 2-(2-amino-2-thiazolin-4-yl)acetic acid or its pharmaceutically acceptable acid addition or cationic salts, as well as its lower alkyl esters, useful in detoxification of certain metal ions in animals, including humans.

In recent years there has been a growing awareness of the importance of trace metals in the environment, many of which are essential to nutrition at appropriate levels but give rise to toxic manifestations if the animal body is exposed to higher levels. The role of chelating agents in medicine (chelation therapy) to remove excessive quantities of metal ions which are producing toxic effects has been reviewed recently by Williams and Halstead, *J. Toxicol.: Clin. Toxicol.*, 19(10), 1081–1115 (1983).

Metals are unique poisons in that they are not subject to metabolic destruction such as occurs for organic poisons. Examples of metals which are essential for nutrition at low levels but toxic in excessive amounts include chromium, cobalt, copper, iron, manganese, molybdenum, selenium and zinc. Less commonly encountered toxic metal ions are those of aluminum, antimony, arsenic, beryllium, nickel, tellurium, thallium and tin, as well as certain radioactive elements. Of course, chelation therapy can also be employed to reduce toxic levels of heavy metals, for example, lead, mercury and cadmium. Chelation therapy is a method of treatment of animals, including humans, which reduces toxic levels of one or more metal ions to a level at which the metal ion is innocuous by administration of one or more chelating agents. Effective chelation therapy depends upon selection of the appropriate chelating agent or combination of such agents, commonly referred to in the art as "ligands". While a number of ligands are known to be useful in chelation therapy, the search for new useful ligands continues.

2-Amino-2-thiazoline has been reported to be useful in protecting animals from exposure to radioactivity, *Chem. Abstr.* 92, 209061q (1980), see also British Pat. No. 1,109,150.

2-Aminothiazol-4-acetic acid is an important intermediate for preparation of certain beta-lactam antibiotics, especially cephalosporins. See, e.g., European Patent Appln. No. 34,340.

SUMMARY OF THE INVENTION

The invention relates to 2-(2-amino-2-thiazolin-4-yl)acetic acid, a pharmaceutically acceptable acid addition or cationic salt, or certain ester precursors thereof, of the formula

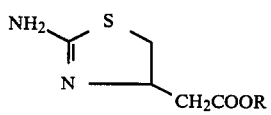

wherein R is H or alkyl having from one to four carbon atoms. Particularly preferred values of R are H, methyl or ethyl and the most particularly preferred compound of formula (I) is 2-(2-amino-2-thiazolin-4-yl)acetic acid, or said salt thereof.

Pharmaceutically acceptable acid addition salts are those prepared by reacting the carboxylic acid or ester of formula (I) with one equivalent of acid. Suitable acids for this purpose are, for example, HCl, HBr, $H_2SO_4$, $H_3PO_4$, $CH_3SO_3H$, p-toluenesulfonic, maleic, fumaric, succinic, or citric acid. For a current list of such acids see, e.g., Berge et al. *J. Pharm. Sci.*, 66, 1–19 (1977).

Pharmaceutically acceptable cationic salts are the carboxylate salts of the acid of formula (I, R is H) and are ordinarily obtained by reacting equivalent amounts of the compound (I), R is H with, e.g., a suitable oxide, hydroxide, carbonate or bicarbonate of the metal. Alternatively, ammonium or amine cationic salts are formed in like manner, e.g., by reacting equivalent amounts of a suitable amine and carboxylic acid of formula (I). Examples of suitable metals and amines for this purpose include sodium, potassium, lithium, calcium, magnesium, zinc, aluminum, ethanolamine, ethylene diamine, diethanolamine, N,N-dibenzylethylenediamine, N-methylglucamine and choline.

The compounds of the invention, especially the carboxylic acid of formula (I) and its pharmaceutically acceptable salts are useful in chelation therapy for reducing toxic levels of trace metals and heavy metals, in animals, including humans, and for protection of the animal body during exposure to radioactivity.

Further, the invention provides a method for reducing a toxic level of a metal ion in an animal in need of such treatment, which comprises administering to said animal a metal ion reducing effective amount of a compound of formula (I) or a pharmaceutically acceptable salt thereof.

Further provided is a pharmaceutical composition comprising a pharmaceutically acceptable carrier and a metal ion reducing effective amount of a compound of formula (I) or a pharmaceutically acceptable salt thereof.

DETAILED DESCRIPTION OF THE INVENTION

The compounds of formula (I) are prepared, for example, by reacting equimolar amounts of thiourea and a lower alkyl ester of 4-bromocrotonic acid as outlined below.

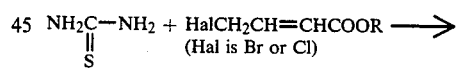

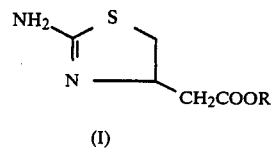

The reaction is preferably carried out in the presence of a reaction inert organic solvent and an acid binding agent. While an equivalent amount of acid binding agent is required by theory to neutralize the hydrogen bromide or hydrogen chloride generated, in practice it is preferred to employ from 2 to 5 equivalents of acid binding agent.

A wide variety of alkaline substances, known to react readily with strong acids, such as hydrogen bromide and hydrogen chloride, can be employed as suitable acid binding agents. Examples of preferred such agents are, sodium bicarbonate, calcium carbonate, trisodium phosphate, potassium citrate, triethylamine, N-methylmorpholine, N-methylpiperidine or N,N-dimethylpiperazine. Sodium bicarbonate is especially preferred for reasons of economy and efficiency.

Examples of reaction-inert organic solvents which can be employed in the above reaction to prepared ethers of formula (I) are lower alkyl ketones such as acetone, methylethyl ketone and methylisobutyl ketone; esters such as ethyl ether, isopropyl ether, ethylene glycol dimethylether, tetrahydrofuran and dioxane; acetonitrile, dimethylformamide and dimethylsulfoxide. Acetone is especially preferred for reasons of economy.

While the reaction may be carried out successfully over a wide temperature range, a preferred temperature is in the range of from 25° to 100° C. For solvents boiling at a temperature within the preferred range it is ordinarily most convenient to carry out the reaction at the boiling point of the solvent. Thus, with the most preferred solvent, acetone, the preferred temperature is 56° C.

The ester of formula (I) obtained by the above reaction can be isolated and purified by standard methods such as by evaporation of the reaction solvent after removal of insolubles by filtration and purification, e.g., by crystallization or by chromatographic methods known in the art. The esters of formula (I) can also be converted to acid addition salts by well known techniques, for example, by contacting a solution of the ester of formula (I) in a non-aqueous solvent, such as ethyl ether, tetrahydrofuran or ethyl acetate; with an equivalent of a pharmaceutically acceptable acid, e.g., hydrochloric acid or citric acid, and isolation of the precipitated salt by filtration or by addition of a nonsolvent e.g., hexane, in the event that a precipitate does not form readily.

While the esters of formula (I) are useful in their own right as agents for use in chelation therapy and for radioprotection, it is ordinarily preferred to convert the esters of formula (I) to the corresponding carboxylic acid, (I), R is H. This is readily accomplished by hydrolysis of the ester. While, the hydrolysis can be carried out under either alkaline or acidic hydrolysis conditions, it is ordinarily preferred to employ alkaline hydrolysis followed by acidification to obtain the desired carboxylic acid of formula (I).

In a typical hydrolysis, the ester of formula (I) is dissolved in an aqueous alcoholic solvent, e.g., aqueous methanol or aqueous ethanol, an equivalent of an alkali metal or alkaline earth hydroxide is added, and the resulting mixture is stirred at or about room temperature until saponification is complete. A preferred hydroxide for this purpose for reasons of economy is sodium hydroxide. Typically the saponification is complete with 2 to 24 hours, after which the resulting solution is acidified, e.g., with hydrochloric acid and the acidified mixture evaporated to dryness to obtain the crude acid addition salt of the acid of formula (I), R is H. The crude material is purified by methods well known in the art, e.g., by dissolving in water, extraction with a water immiscible solvent to remove non-polar impurities, and evaporation of the aqueous layer.

Alternatively, the aqueous solution of acid addition salt, e.g., hydrochloride salt, can be adjusted to the isoelectric point by careful addition of alkali, e.g., dilute sodium hydroxide solution, until precipitation commences. The precipitated amino acid, is then collected by filtration of the cooled mixture.

The cationic salts of the carboxylic acid of formula (I) are obtained by standard methods well known in the art, for example, a solution of the amino acid of formula (I) or its acid addition salt is treated with a sufficient amount of the desired base to convert either of the starting compounds to the desired cationic salt. For example, addition of one equivalent of potassium hydroxide to a solution of the amino acid affords the corresponding potassium salt, (I), R=K. Addition of two equivalents of potassium hydroxide to a solution of the hydrochloride addition salt of the carboxylic acid of formula (I) affords the same potassium salt.

The compounds of the invention contain a chiral center at the 4-position of the thiazoline ring and the invention includes both the resolved and unresolved forms.

Toxicity in humans due to high levels of metal ions in vivo may be due to one or more causes. For example, toxicity may occur from exposure to heavy metals from the metal refining industry, additives for petroleum products, pesticides, and to various metals used in modern industry. While metal toxicity is often an acute malady, chronic toxic effects have been indicated to be involved in certain types of cancers, arthritis and other diseases which are more common in industrialized nations.

The compounds of formula (I) are useful in removal of all or a part of a particular metal ion from animals, including humans. The invention compounds are useful in reducing toxic levels of certain heavy metal and trace metal ions from said animals by virtue of their ability to form highly stable complexes with said metal ions which enhance excretion of the unwanted metal. Metals, the ions of which can be removed from animals by administration of an invention compound, include, for example, aluminum, antimony, arsenic, cadmium, chromium, cobalt, copper, iron, mercury, manganese, molybdenum, lead, selenium, tin, vanadium and zinc. The invention compounds are particularly effective in removal of polyvalent ions of antimony, copper, manganese, mercury, lead and zinc.

The in vivo evaluation of the invention compounds is carried out, for example, by exposure of animals such as fish, oysters, mice or rats to toxic levels of a given metal until symptoms of toxicity due to the metal are observed. This is followed by administration of the test compound, e.g., in the feed of fish or oysters, or when mammals such as mice or rats are employed, the drug is given by either the oral, intraperitoneal or intravenous route of administration in single or multiple doses. In each case, the animals are observed for changes which may occur, rate of survival and excretions may be monitored, in order to determine the efficacy of the drug. Comparison is made with untreated control groups to which metal ion, but no drug, is administered; and optionally with normal controls (no metal ion, no drug).

For human use in chelation therapy the compound of formula (I) is administered alone or in combination with pharmaceutically acceptable carriers or diluents, in ether single or multiple doses. Suitable pharmaceutical carriers include inert diluents or fillers, sterile aqueous solutions and various organic solvents. The pharmaceutical compositions formed by combining the novel compounds of formula (I) or salts thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubrication agents such as sodium lauryl sulfate and talc are often useful for tableting purposes. Solid compositions of a similar type may also be employed as fillers in soft and hard filled gelatin capsules. Preferred materials therefor include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents together with diluents such as water, ethanol, propylene glycol, glycerin, or combinations thereof.

Preferably, the products of this invention are administered orally in unit dosage form, i.e., as a single physically discrete dosage unit containing an appropriate amount of the active compound in combination with a pharmaceutically acceptable carrier or diluent. Examples of such unit dosage forms are tablets or capsules containing from about 25 to 1,500 mg. of the active ingredient, the compound of formula (I) comprising from about 10% to 90% of the total weight of the dosage unit.

For parenteral administration, solutions or suspension of the compound of formula (I) in sterile aqueous solutions, for example aqueous propylene glycol, sodium chloride, dextrose or sodium bicarbonate solutions are employed. Such dosage forms are suitably buffered if desired. The preparation of suitable sterile liquid media for parenteral administration will be well known to those skilled in the art.

To alleviate the toxic symptoms of certain metal ions in animals, including humans, the compounds of formula (I) are administered by a variety of conventional routes of administration including orally and parenterally. Preferably, the compounds are administered orally. In general, these compounds will be administered orally at doses between about 0.5 and 50 mg./kg. body weight of the subject to be treated per day, preferably from about 1.0 to 30 mg/kg. per day, in single or divided doses. If parenteral administration is desired, then these compounds can be given at total daily doses between about 0.5 and 10 mg/kg. body weight of the subject to be treated. However, at the discretion of the attending physician, some variation in dosage will necessarily occur, depending upon the condition of the subject being treated and the particular compound employed.

The present invention is illustrated by the following examples. However, it should be understood that the invention is not limited to the specific details of these examples. All temperatures are in degrees centigrade. Nuclear magnetic resonance spectra (NMR) were measured for solutions in deuterated chloroform (CDCl$_3$), deuterated methanol (CD$_3$OD) or deuterated dimethyl sulfoxide (DMSO-d$_6$), and peak positions are reported in parts per million downfield from a tetramethylsilane internal standard. The following abbreviations for peak shapes are used: bs, broad singlet, s, singlet; d, doublet; t, triplet; q, quartet, m, multiplet.

EXAMPLE 1

2-(2-Amino-2-thiazolin-4-yl)acetic Acid Hydrochloride

A solution of 9.3 g. (0.05 mole) methyl 4-bromocrotonate, 3.9 g. (0.05 mole) thiourea and 8.4 g. (0.10 mole) sodium bicarbonate in 200 ml. acetone was heated at reflux for two hours. The resulting mixture was filtered and the filtrate evaporated at reduced pressure to yield 10.0 g. of crude methyl 2-amino-(2-thiazoline)-4-acetate. The methyl ester was dissolved in 60 ml. of 20% (w/w) aqueous methanol, heated with 2.3 g. (0.05 mole) sodium hydroxide and stirred at room temperature for 18 hours. The resulting solution was acidified (pH 1.0) with 6N hydrochloric acid and evaporated to dryness. The solid residue was dissolved in water and washed with methylene chloride. The aqueous layer was separated and evaporated in vacuo to afford a residual oil which solidified upon trituration with acetone to yield 4.5 g (56%). The solid was taken up in methanol, treated with activated carbon, filtered and the filtrate evaporated to give 3.2 g. (40%) of the title compound, M.P. 177°–179° C. Infrared (KBr) cm$^{-1}$: 1610, 1660, 1720, 3100–2600; $^1$H-NMR (D$_6$-dimethylsulfoxide) ppm (delta): 2.70 (d, 2H), 3.45 (m, 3H), 3.70 (m, 1H), 4.48 (m, 1H); Mass spectrum (m/e): 159.9 (M+).

Use of sulfuric acid or hydrobromic acid in place of 6N hydrochloric acid for acidification to pH 1.0 in the above procedure affords the corresponding hydrogen sulfate or hydrogen bromide acid addition salts in like manner.

EXAMPLE 2

Use of ethyl 4-bromocrotonate in place of the corresponding methyl ester in the procedure Example 1 affords ethyl 2-(2-amino-2-thiazolin-4-yl)acetate as an intermediate which is hydrolyzed to 2-(2-amino-2-thiazolin-4-yl)acetic acid as the hydrochloride salt.

In like manner use of the n-propyl, isopropyl, n-butyl, isobutyl or secondary butyl ester of 4-bromocrotonic acid in the procedure of Example 1 affords the corresponding ester of the formula

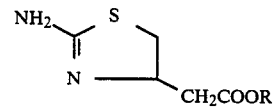

wherein R is n-propyl, isopropyl, n-butyl, isobutyl or secondary butyl. These esters are hydrolyzed to the amino acid (R=H) hydrochloride in like manner.

EXAMPLE 3

2-(2-Amino-2-thiazolin-4-yl)acetic acid

A solution of 1.965 g. (0.010 mole) 2-(2-amino-2-thiazolin-4-yl)acetic acid hydrochloride in 150 ml. water is titurated with an equimolar amount of 1.0N sodium hydroxide solution. The resulting mixture is stirred with cooling at 5° C. for two hours then filtered. The sodium salt is washed with cold water, ethanol and dried.

EXAMPLE 4

Sodium 2-(2-Amino-2-thiazolin-4-yl)acetate

The above procedure was repeated but two equivalents of 1.0N sodium hydroxide solution is added and the water evaporated in vacuo. The residue is triturated with ethanol and filtered to obtain the desired sodium salt.

The potassium salt is obtained by employing potassium hydroxide in this procedure.

I claim:

1. A compound of the formula

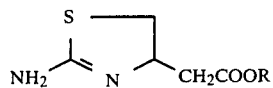

or a pharmaceutically acceptable acid addition or cationic salt thereof, wherein R is H or alkyl having from one to four carbon atoms.

2. The compound according to claim 1: methyl 2-(2-amino-2-thiazolin-4-yl)acetate.

3. The compound according to claim 1: ethyl 2-(2-amino-2-thiazolin-4-yl)acetate.

4. The compound according to claim 1: 2-(2-amino-2-thiazolin-4-yl)acetic acid.

* * * * *